United States Patent
Crockford (12)

(10) Patent No.: US 6,637,305 B2
(45) Date of Patent: Oct. 28, 2003

(54) APPARATUS FOR MACHINING COMPOSITE MATERIAL TEST SPECIMENS

(76) Inventor: William Crockford, 13066 S. Dowling Rd., College Station, TX (US) 77845

( * ) Notice: Subject to any disclaimer, the term of this patent is extended or adjusted under 35 U.S.C. 154(b) by 0 days.

(21) Appl. No.: 10/072,476

(22) Filed: Feb. 7, 2002

(65) Prior Publication Data

US 2003/0145696 A1 Aug. 7, 2003

(51) Int. Cl.⁷ .................................................. B23B 5/00
(52) U.S. Cl. ......................................................... 82/117
(58) Field of Search ........................... 82/117, 120, 119, 82/121, 122, 124, 165

(56) References Cited

U.S. PATENT DOCUMENTS

| | | | |
|---|---|---|---|
| 4,675,825 A | * | 6/1987 | DeMenthon ................. 364/474 |
| 5,316,416 A | | 5/1994 | Kim |
| 5,319,983 A | * | 6/1994 | Brown et al. ................. 73/799 |
| 6,186,248 B1 | | 2/2001 | Silay et al. |
| 6,272,956 B1 | | 8/2001 | Schuttel |
| 6,299,179 B1 | | 10/2001 | Sheffer |
| 6,311,684 B1 | | 11/2001 | Hodsden et al. |

* cited by examiner

Primary Examiner—Willmon Fridie, Jr.
(74) Attorney, Agent, or Firm—McHale & Slavin, P.A.

(57) ABSTRACT

This application is drawn toward a combined coring and sawing machine for composite materials. The preferred embodiment combines the functionality of two machines typically used in the prior art and minimizes both the cost and errors associated with larger cutting tools, e.g. diamond cutting devices, used in the prior art. Combining variable speed motor operation with pressure actuated advancement of cutting tools and automatic workholding actuation provides a system which is effectively open-loop "load" controlled as opposed to the open-loop "displacement" control systems most often used in the prior art. Simple and economical specimen ejection techniques are a further improvement over the prior art which often includes no ejection facility at all.

2 Claims, 5 Drawing Sheets

US 6,637,305 B2

APPARATUS FOR MACHINING COMPOSITE MATERIAL TEST SPECIMENS

FIELD OF THE INVENTION

This invention relates to material machining devices; particularly to machining device comprising in combination coring, sawing and positioning means; and most particularly to such devices as are used to machine samples of composite materials such as asphalt concrete into solid right circular cylindrical test specimens of smaller dimensions or beams of rectangular cross section.

BACKGROUND OF THE INVENTION AND DISCUSSION OF PRIOR ART

Composite materials, in particular those which have very hard inclusions in a relatively soft binder (e.g. carbon fiber in an epoxy matrix or rock in an asphalt matrix), are difficult to machine into acceptable specimens for subsequent measurement of their engineering properties under loading conditions.

The reason for this is two-fold:

(1) the binders are usually temperature dependent similar to polymers; and (2) the usual methods are subject to errors because of the types of machines used.

As an illustrative, albeit non-limiting embodiment, the case of asphalt concrete will be further explored. Asphalt concrete is a mixture of a binder material and rock typically used in pavement construction. The most common material of this type is mixed and compacted while hot. In order to test the material for its engineering properties such as strength or modulus or Poisson's ratio, the mixed and compacted material must be cooled and cut into a shape and surface smoothness suitable for instrumentation and testing. Water and/or extended periods stored in a refrigerator are the most common methods of cooling. Water may cool faster, but asphalt mixtures are sometimes adversely affected by the water, and wet surfaces may not be acceptable for the testing instrumentation method of choice. Cooling is generally required prior to cutting in order to maintain specimen shape during handling and clamping. Fundamentally, the cooling stiffens the material and makes the polymer-like binder component stiffness closer to the stiffness of the rock component of the composite material. Additional cooling and/or cleaning is generally required during the cutting operation for chip/dust removal. Even when cooled, there is still a difference in stiffness between the rock and the asphalt. In many cases, it is also true that the oversize compacted sample of the material has a variation in its fundamental properties such as air voids from one end to the other and from the center to the outside periphery on the radius. The variation is mostly near the outer compacted surfaces so that coring and sawing of a smaller test specimen from a compacted specimen of a larger first size/dimension often results in the smaller specimen having a more consistent (i.e. less variable) distribution of fundamental properties such as air voids.

A standard lathe type machine cannot effectively be used to remove the center core by single point cutting tool machining of the outer portion of the radius because the cutting tool will damage the material when it hits hard inclusions and those hard inclusions try, in turn, to break chemical and mechanical bonds with the asphalt material. The advantage that coring possesses for this reduction in diameter is that it uses diamond segments or a continuous diamond ring and the material on both sides of the ring is confined, so the damage from the cutting tool is minimized.

The most common shape for a test specimen of this material is a solid right circular cylinder. In order to obtain consistent surface textures and void distribution within the specimen, the cylinder is usually subjected to two cutting operations with relatively expensive diamond cutting tools such as those described by Kwang (U.S. Pat. 5,316,416 May 31, 1994). One cutting operation consists of coring of the circular cross section and the other cutting operation consists of cutting the ends such that they are parallel. The two cutting operations occur in whichever order is convenient and they are usually done with two different machines.

The coring operation is typically performed with a motor driven core barrel which is attached only at one end by a threaded component such as a nut welded to the back of the barrel. Usually the barrel is too long for the application because off-the-shelf core barrels and their mounting system are designed to core into thick pavement structures. This often leads to relatively large run-out and poor surface texture of the cored specimen. Even when using water as the cutting fluid, it is often found that the coring operation ends with the cut specimen lodged inside the core barrel causing some difficulty in removing the good specimen from the barrel since it must come out of the barrel from the same end that it went in.

The specimen ends are usually cut with a motor driven diamond saw. Typically, very large diameter blades are used (e.g. 14–24 inch diameter blades are often used on 4–6 inch diameter specimens). Since the starting sample may not be very much oversize in the length dimension, the sawing operation often takes place very close to the finished ends. Such processing generally results in unacceptable finished ends because the waste end cannot be gripped while sawing, and the large diameter saw blade tends to flex. Some saws have a single blade, others have two blades on a mandrel to simultaneously cut both ends and to try to ensure parallel ends in the finished product. U.S. Pat. No. 6,311,684 issued to Hodsden (Nov. 6, 2001) addresses the issue of reducing the diameter across which a saw must cut, however the stiffness of the wire saw loop in the out of plane direction is likely to result in unacceptable cut surfaces.

In both coring and sawing, the machines currently in use often have difficulty with holding the specimen and feeding the cutter into the specimen (or feeding the specimen into the cutter if the machine design requires that). Specimen clamping is usually accomplished with a standard parallel jaw vise or a "V" jaw on one side of the vise. In order to grip the specimen tight enough to resist the cutter throughout the cutting process, these methods often require clamping forces which result in damage to the specimen.

Potential solutions to this problem include fluid or pneumatic chucks such as those described in U.S. Pat. Nos. 6,299,179 issued to Sheffer (Oct. 9, 2001) and 6,272,956 issued to Schuettel (Aug. 14, 2001). However, fluid chucks have two notable disadvantages: they have an affinity for damaging abrasive particles especially if the fluid is hydraulic oil, and they are often manufactured so that a large piece cannot extend through the back of the chuck because the fluid pressure source and actuating mechanism are often positioned in this location to provide for axial actuation of the jaw mechanism.

The rotational speed of the motor driving the core barrel or the saw, and the feed rate of the cutter into the material being cut are interrelated components of the cutting operation that control the surface finish, accuracy, and precision of the final specimen. In many cases, the drive motor speed is fixed, and the feed control is either manual or done at a fixed rate. Improvements in the drilling operation have been provided by U.S. Pat. No. 6,186,248 issued to Silay & McKinley (Feb. 13, 2001), which teaches a closed loop control system for diamond core drilling that automatically controls penetration rate, weight on the drill bit and torque load applied to the drill string. This device fails to teach or suggest a device for coring and slicing of a specimen.

Thus, the disadvantages which exist in the prior art include the following:

1. Two separate machines are usually necessary to perform the two tasks of coring and slicing. This increases operator involvement in the preparation process and generally results in added costs in initial capital outlay, maintenance, and specimen preparation time.
2. Standard core barrels and saw blades are typically larger and more expensive than necessary to handle the task of cutting engineering test specimens. Not only is this unnecessary, the larger size can cause poor finished specimen geometries.
3. Typical clamping systems tend to induce specimen damage.
4. Because asphalt mixtures vary widely in their composition (e.g. in terms of the rock size and distribution, and the character of the binder), constant RPM motors are not appropriate unless some form of variable speed transmissions are also part of the machine.
5. Again, because of the widely varying composition of asphalt mixtures, manual and constant rate feed systems are not appropriate.

SUMMARY OF THE INVENTION

A material processing machine is presented comprising, in combination, at least one power generating means, which may be illustrated as a motor having varying properties, for example a single reversible variable speed motor and/or variable torque motor. Said motor will generally include a single drive shaft which, in one embodiment, allows optional mounting of three relatively inexpensive small diameter diamond saw blades adapted for cutting beams of rectangular cross section and transfers power to a bearing mounted work holding chuck, the work holding jaws of said chuck being centrifugally and torsionally actuated to contact the specimen, an actuator that moves an open-backed core barrel into the specimen held in the chuck, a finished test specimen and waste material ejection system, and actuators for advancing diamond segmented cutoff tools into the turning specimen held in the chuck.

Accordingly it is an objective of the instant invention to provide an apparatus for machining material with hard inclusions which obviates the disadvantages of prior machines.

It is a further objective of the instant invention to provide a device which is compact in size, enabling it to be used in crowded laboratories or for mobile applications.

It is a further objective of the instant invention to teach a device which combines the processes of coring and sawing the ends of a specimen into one machine.

It is still an additional objective of the instant invention to provide a device in which non-rotating cutting tools are advanced into the oversize sample to cut a cylindrical specimen of the required dimensions.

It is another objective of the instant invention to provide mounting means for optionally installing at least three rotating saw blades adapted for machining rectangular cross section beams at least two at a time, which can be made relatively economically, and which can be easily operated.

Still further objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
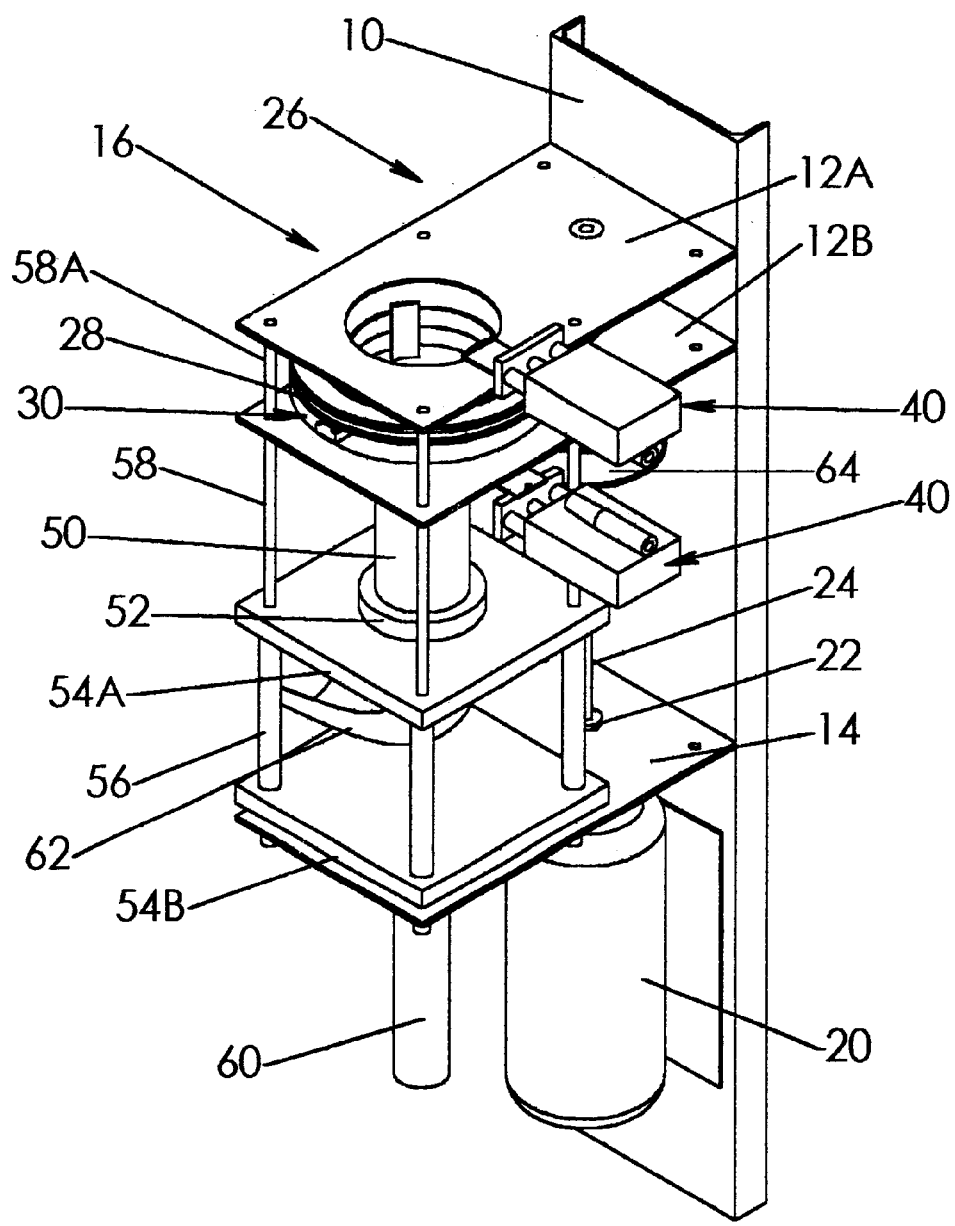
FIG. 1 is an overall perspective view of a material processing machine according to the invention.

Now with reference to FIG. 1, an overall perspective view of a material processing machine according to the invention shown in the preferred orientation in which an oversize sample is placed into the chuck 30 from above and ejection of the finished specimen through the ejection chute 62 is aided by gravity. The entire apparatus may be enclosed in a safety cabinet with positive air flow, illustrated as being from right to left into a cyclonic vacuum and dust bagging system which is not the subject of this invention. Frame 10 is used as the basic building and support means/structure on which to mount the motor 20 and the three plates 12A, 12B and 14. The spacing between plates 12A and 12B is governed by the desired preload on the tapered roller bearings 32 and set by the shaft length 58A. These two plates also function as mounting location devices for bearings 32 and 22. Plate 14 functions as a mounting plate for the actuator 60, the lower end driveshaft bearing 22 and the linear motion shafting 58. A core barrel 50 is mounted to a plate 54A, said plate attached to a push plate 54B with tubular bushings 56 that enable nonrotational linear movement on shafting 58. The core barrel also incorporates a ring 52 of solid or spring-like material that partially ejects the waste material from the chuck at the end of the machining process. A chute 62 directs the finished specimen out to the side for easy access by the operator.

Figure 2:
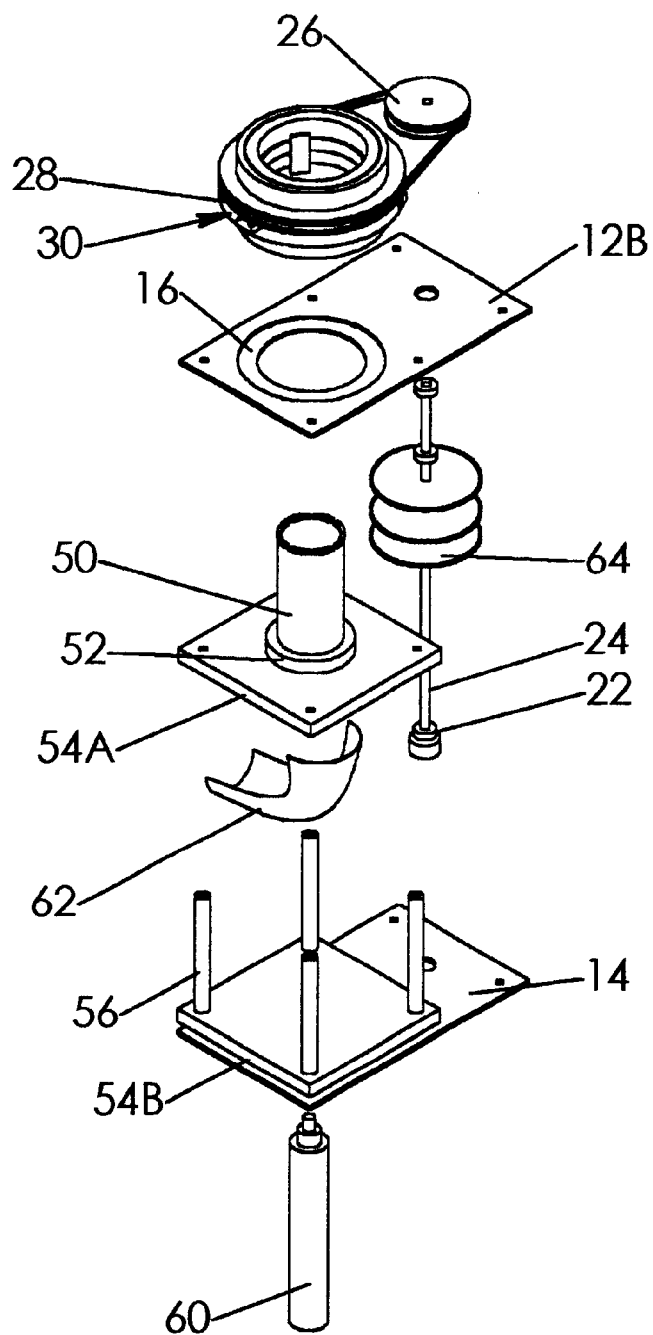
FIG. 2 is an enlarged view of power transmission components hidden from view in FIG. 1.

Now referring to FIG. 2, various components of the power transmission means 26 hidden from view in FIG. 1 are illustrated. The motor 20 rotates driveshaft 24 on which is mounted the pulley 26. Power is transmitted to the scroll drive plate 34 using a belt 28. Taper bearings 32 are axially located in a bearing recess 16. Optional saw blades 64 may be mounted on the driveshaft for direct drive cutting of long beams manually or automatically power fed through the blades.

Figure 3:
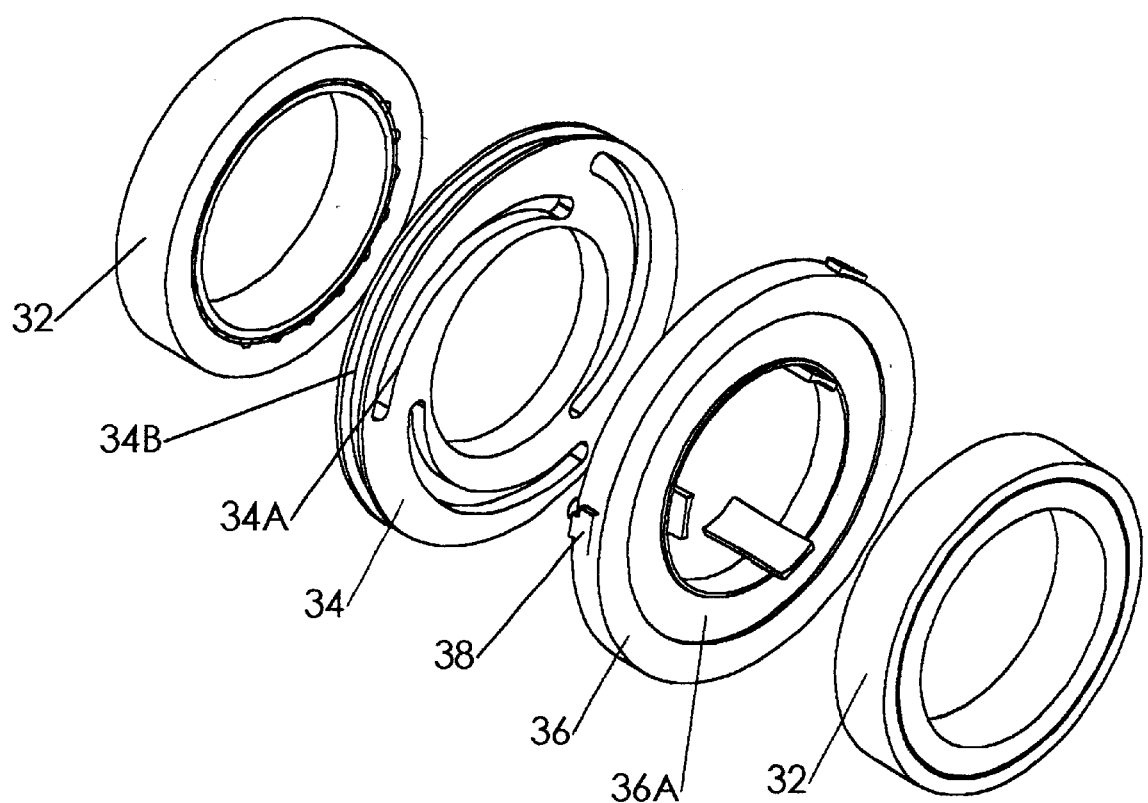
FIG. 3 is an enlarged, fragmented perspective view of a centrifugal chuck.

With reference now to FIG. 3, a centrifugal chuck 30 is used to advance and retract the workholding jaws 38, the direction of movement of the jaws controlled by the direction of rotation of the motor 20; and the pressure applied to the specimen by the workholding jaws controlled by a combination of the pressure in actuator 60, the preload on the chuck bearings 32, and the applied torque. The jaw bearing race 34A receives the jaw bearing 38C so that differential rotational movement between the jaw guide plate 36 and the scroll drive plate 34 caused by inertial and torsional effects causes the jaw arm 38A to move radially inward or outward in the "t-slot". The chuck receives its rotational power through the power transmission belt groove 34B.

Figure 4:
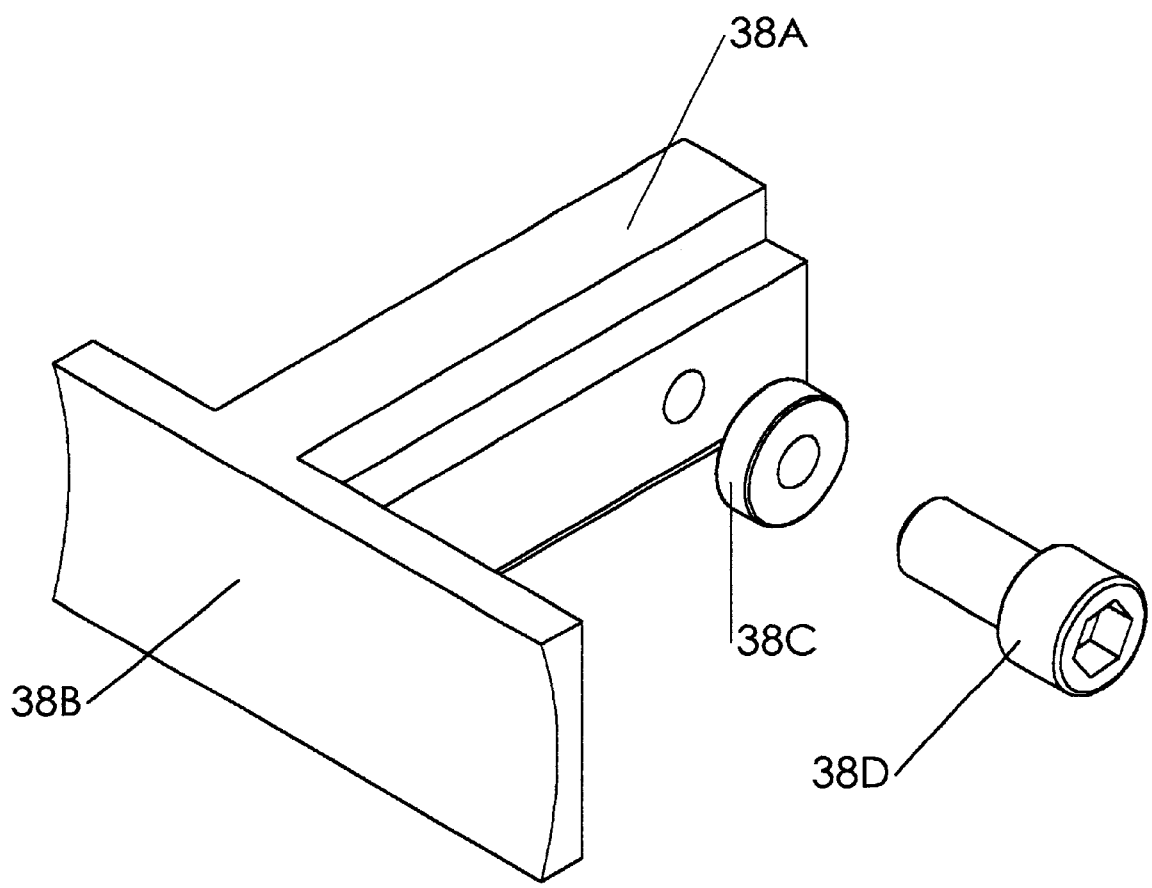
FIG. 4 is an enlarged, fragmented perspective view of a chuck jaw assembly.

As illustrated in FIG. 4, a centrifugal chuck jaw assembly is described wherein the jaw assembly comprises a "t-shaped" cross section arm 38A, a contact pad 38B that is, in a preferred embodiment, preferably machined to the radius of the sample being machined, and a bearing 38C that is attached to the arm by an attachment means 38D. The t-shaped cross section of the jaw and the t-slot in the jaw guide plate 36 ensure that the contact pad 38B maintains axial alignment of the sample during machining.

Figure 5:
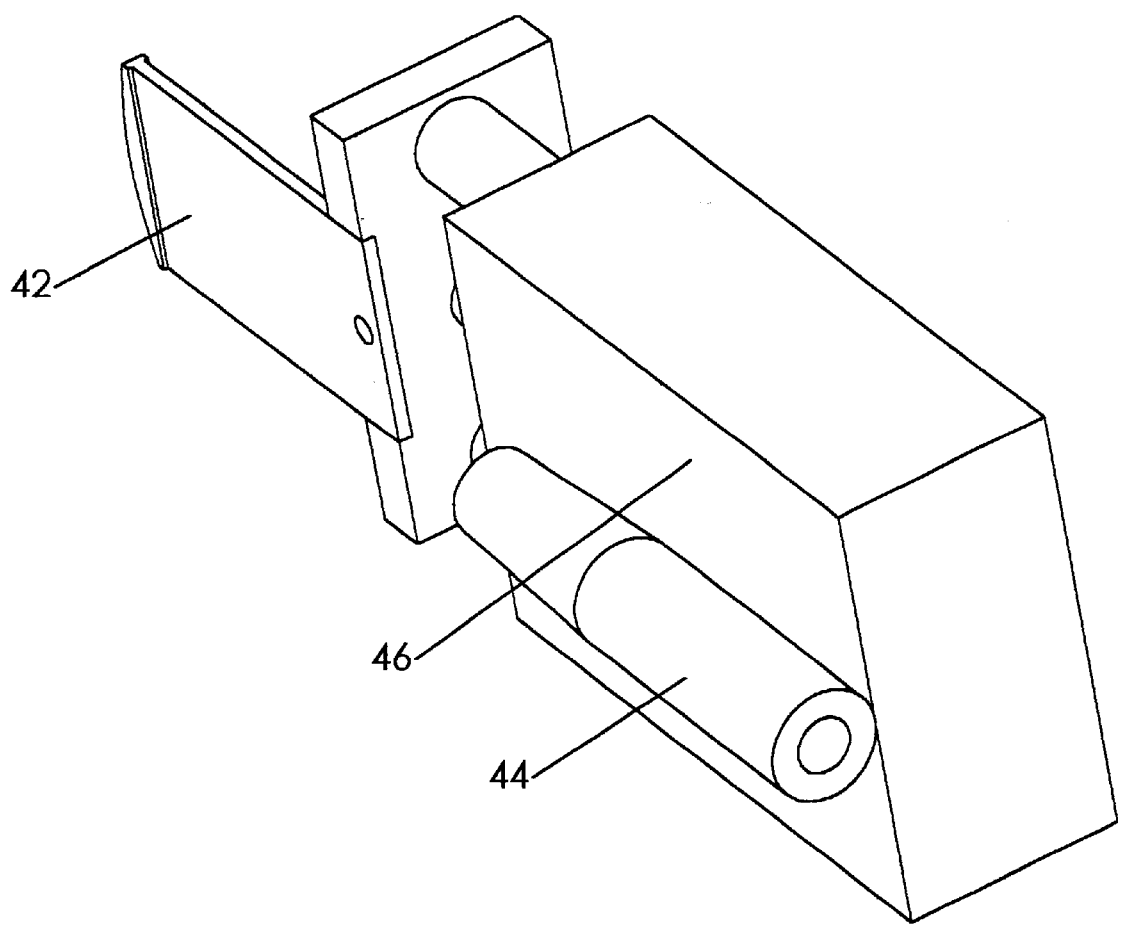
FIG. 5 is an enlarged perspective view of a cutoff tool.

As illustrated in FIG. 5, a diamond segment cutoff tool 42 is advanced into the turning specimen by a guided pneumatic actuator 46 which prevents misalignment of the tool as it advances into the work. A cooling nozzle 44 attached to an air supply is used to supply the cutting "fluid". While virtually any type of cooling nozzle may be used, in a preferred embodiment the cooling nozzle utilizes-the vortex generator technology of ARTX, Ltd.

The primary purpose of the instantly disclosed machine is to cut a cylindrical test specimen from a larger cylindrical specimen. In the preferred embodiment, large diameter saw blades usually used to cut the ends of a rigidly clamped non-rotating specimen are avoided by using the concepts of single point tool machining. In this system, the cutting tool is advanced into the turning workpiece and the depth of required cut is reduced by a factor of two since the tool must only be advanced a distance equal to the radius of the specimen instead of the diameter. Assuming the same cross section of the cutting tool, the shorter distance of cut translates into better finish and overall tolerances of the cut. In order to reduce chucking operations and possible damage to the finished specimen, the preferred, albeit non-mandatory order of operation is to cut the ends of the specimen first and core it second. This requires a slightly longer cutoff tool that would be necessary if the order were reversed because it will be cutting though some material on the radius that will become waste material after the coring operation, but it considerably simplifies the machine design and reduces the potential for specimen damage. While not wishing to be limited to any particular set of operating parameters or conditions, as a point of reference, a typical finished specimen will be of an average diameter of about 100–104 mm, with a standard deviation of not more than about 1 mm, a height of about 147.5–152.5 mm, an end flatness of about 0.3 mm and an end parallelism of about 1°.

The basic steps for machining a cylindrical test specimen are as follow:

1) With the machine turned off, and the core barrel positioned in a lowered position, place a sample in the chuck resting on the upper (cutting) end of the core barrel;
2) Turn the machine on in the direction of rotation required for the chuck jaws to grip the specimen. When the machine starts turning the chuck, two things will cause the jaws to advance inward: (a) the inertia of jaw guide plate 36 will cause it to lag behind the scroll drive plate 34 causing the jaws to start moving inward due to the scroll shape of the races 34A, and (b) when the jaws come into contact with the outer diameter surface of the sample of material, the friction at the core barrel cutting bit will cause a torque reaction that will further tighten the jaws against the specimen;
3) Apply pneumatic pressure to the cutoff tools 40 which will apply further torque reaction even if the core barrel is further retracted to eliminated contact with the bottom of the specimen. Maintaining pressure will continue to advance the cutoff tools until reaching the center of the specimen. It is important that this tool advancement be done with pressure or force control methodology instead of displacement control methodology because of the inhomogeneous nature of these composite materials. The actuator is subsequently retracted after completion of the cut to center;
4) Upon completion of the cutoff operation, pressure is applied to the extend side of actuator 60. This will reapply a torque reaction with the core barrel and begin cutting the core. This cutting will continue while maintaining constant pressure until the core has been cut through the sample;
5) Upon reaching the end of the cored length, the finished test specimen will drop out the lower end of the core barrel and be ejected by gravity through the chute 62. At this point, the motor should be turned off. This automatic specimen drop out is an advantage of the current embodiment. Core barrels are normally built with the diamond segment overhanging the tube barrel to which it is attached on both the inside and outside diameters. By using a bottom actuated, upward advancing core barrel, instead of the conventional method of coring from the top down, the preferred embodiment takes advantage of the clearance between the newly sawn core and the inside diameter of the tube to obtain an easy release of the specimen from the core barrel. If the specimen is cored from the top as is almost exclusively done in the prior art, since there is little or no clearance between the inside diameter of the diamond segments and the outside diameter of the cored specimen, it is often difficult to remove the specimen from the core barrel after the cut, especially if the cutting fluid has done a poor job of removing chips and waste material;
6) With pressure still applied to actuator 60, the motor is turned back on in the reverse direction. During this operation, the ring 52 will be in contact with the bottom of the waste material annulus which will generate a torque reaction that will cause initial release of the jaws of the chuck and inertial effects should then take over to fully retract the jaws into the chuck body. The operator will turn off the motor when the jaws are fully retracted, but leave the pressure applied to actuator 60. When plates 54A and 12B are in contact or very close to being in contact, the waste annulus will be sufficiently above the top of the chuck to manually or automatically remove and discard it;

7) Lastly, repositioning of the actuator 60 to a lowered position prepares the machine to repeat the process for the next specimen.

Machining a beam merely involves feeding the sample through the rotating saw blades, cutting two beams from one sample on the first cut and then refeeding the beams through the appropriate blade position to obtain the desired rectangular cross section. It is noted that spacing between the saw blades need not be equal. In many beam fatigue devices, the beam is required to be rectangular. By setting the blades at independent distances, one from the other, two beams of rectangular cross section may be cut by making a first pass, rotating the core a quarter revolution, and then making a second pass.

While a preferred mode of operation has been described above, various alternative embodiments are nevertheless contemplated.

In the preferred embodiment, pneumatic actuators 46 and 60 are shown for advancing the cutting tools into the work. The actuators may be of a different type, such as hydraulic or mechanical. However, hydraulic actuators may experience increased operating difficulty in this dirty abrasive environment and mechanical actuators tend to be displacement rate controlled, not pressure controlled, and are therefore less desirable in this application.

There is no significant difference between the operation of the preferred and alternative actuator embodiments, except for the limitations noted in the description.

Regarding the operation of the cutters, diamond cutters 42 and 50 may be replaced by other cutting materials depending on the type of material in the specimen. High speed miniature rotational cutters may be used in place of the fixed diamond segments if the rotational drive mechanisms are small enough or the cutter kerf is big enough to accommodate the drive mechanism. In general, miniature cutters currently available are unlikely to be capable of meeting the needs of certain industries, e.g. the asphalt industry.

Cutter operation with alternative means is not significantly different from that given in the preferred embodiment.

Now with reference to power transmission, the preferred embodiment comprises direct drive of optional saw blades and belt drive of the workholding chuck. Several common alternative methods are available for driving the workholding chuck, including gears, cog belts, or hydraulic motors. Direct drive of the workholding chuck is not economically feasible because of the relatively large diameter of the chuck and the need to be able to access it from both ends (i.e. from the top by an operator and from the bottom by the core barrel system). Belt drive was chosen as the preferred embodiment because there may be situations during operation in which it might actually be beneficial for the belt to slip and the belt is probably less susceptible to damage from the abrasive environment than either lubricated gears or hydraulic motors.

There is no significant difference in operation of the invention with alternative embodiments other than the limitations noted.

As illustrated in the preferred embodiment, a workholding chuck is shown which allows access from either end. This is a critical feature that is governed by the desire to cut both ends of the specimen simultaneously without the need to rechuck the sample. There are many fluid power chucks in the prior art. However, the inventor is unaware of any in which both ends of the chuck are accessible. An alternative embodiment contemplated by the instant invention includes a fluid chuck that introduces the fluid through a sealed radial ring. Such a chuck would need to have a stationary outer ring that introduces the fluid under pressure, maintains a seal, and provides concentricity of the elements of the device. Manual chucks (e.g. key drive scroll chucks) commonly used on inexpensive manual lathes are not appropriate for this application as there is a need for the chuck to be self-tightening during operation due to potential creep of the material under the workholding jaws.

Operation of alternative chuck embodiments is not significantly different from the preferred embodiment except with regard to cleanliness. Hydraulic fluid chucks must be kept free of abrasive dust particles for proper operation. Pneumatic versions of fluid chucks would be preferred over hydraulic oil versions.

With regard to the specimen ejection system, the preferred embodiment relies primarily on gravity to eject the finished specimen from the bottom of the chuck and uses an actuator to partially eject the waste outer ring of material from the top of the chuck. An actuator or mechanical spring system could also be used on the top of the specimen to force the finished specimen out the bottom of the chuck after completion of the cutting operation.

Operation of alternative ejection embodiments is not significantly different from the preferred embodiment.

It can be seen that a combined coring and sawing machine for composite materials is provided according to the invention. The preferred embodiment combines the functionality of two machines typically used in the prior art and minimizes both the cost and errors associated with larger diamond cutting tools used in the prior art. Combining variable speed motor operation with pressure actuated advancement of cutting tools and automatic workholding actuation provides a system which is effectively open-loop "load" controlled as opposed to the inferior open-loop "displacement" control systems most often used in the prior art. Simple and economical specimen ejection techniques are an improvement over the prior art which often includes no ejection facility at all.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

One skilled in the art will readily appreciate that the present invention is well adapted to carry out the objects and obtain the ends and advantages mentioned, as well as those inherent therein. The methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims. It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A material machining device comprising:

a frame supporting at least one power generating means;

at least one power transmitting means connected to said power generating means;

rotatable workholding means connected to said power transmitting means for holding a rotating workpiece specimen, said specimen substantially defining a right circular cylindrical shape of a first dimension; and at least one cutter means connected to said power transmitting means for advancing into a rotating workpiece specimen for cutting said specimen, wherein said at least one power generating means connected to said at least one power transmitting means provides variable movement to said workpiece;

whereby a right circular cylinder test specimen of a second and lesser dimension is produced, said test specimen having a dimension and finish suitable for subsequent engineering material property testing.

2. A material machining device of claim 1 comprising said at least one cutter means advancing a distance approximately equal to the radius of said right circular cylindrical shape of said rotating workpiece specimen.

* * * * *